US009526746B2

(12) United States Patent
Kemp et al.

(10) Patent No.: US 9,526,746 B2
(45) Date of Patent: Dec. 27, 2016

(54) WOUND HEALING COMPOSITION

(75) Inventors: Paul Kemp, Romiley (GB); Györgyi Talas, Timperley (GB); Jennifer Sutherland, Stockport (GB); Margaret Batten, Whiston (GB); Penelope Ann Johnson, Glossop (GB); Andrew Shering, Chorlton (GB); Michael McWhan, Glossop (GB)

(73) Assignee: SMITH & NEPHEW, INC., Memphis, TN (US)

( * ) Notice: Subject to any disclaimer, the term of this patent is extended or adjusted under 35 U.S.C. 154(b) by 2359 days.

(21) Appl. No.: 10/589,227

(22) PCT Filed: Feb. 14, 2005

(86) PCT No.: PCT/GB2005/000523
§ 371 (c)(1),
(2), (4) Date: Jul. 2, 2007

(87) PCT Pub. No.: WO2005/079822
PCT Pub. Date: Sep. 1, 2005

(65) Prior Publication Data
US 2008/0226720 A1 Sep. 18, 2008

Related U.S. Application Data

(60) Provisional application No. 60/556,194, filed on Mar. 25, 2004, provisional application No. 60/556,155, filed on Mar. 25, 2004, provisional application No. 60/632,425, filed on Dec. 1, 2004.

(30) Foreign Application Priority Data

Feb. 13, 2004 (GB) .................................. 0403220.7
Feb. 13, 2004 (GB) .................................. 0403226.4
Nov. 30, 2004 (GB) .................................. 0426252.3

(51) Int. Cl.
| *A61K 35/12* | (2015.01) |
| *A61K 9/00* | (2006.01) |
| *A61P 17/02* | (2006.01) |
| *A61K 35/33* | (2015.01) |
| *A61K 35/34* | (2015.01) |
| *A61K 35/36* | (2015.01) |
| *A61L 27/38* | (2006.01) |
| *A61L 27/60* | (2006.01) |
| *G01N 33/569* | (2006.01) |
| *A61K 45/06* | (2006.01) |

(52) U.S. Cl.
CPC ............... *A61K 35/33* (2013.01); *A61K 35/34* (2013.01); *A61K 35/36* (2013.01); *A61K 45/06* (2013.01); *A61L 27/3804* (2013.01); *A61L 27/3895* (2013.01); *A61L 27/60* (2013.01); *G01N 33/56966* (2013.01)

(58) Field of Classification Search
CPC .... A61K 35/36; A61K 2300/00; A61K 35/33; A61K 35/34; A61K 45/06; A61L 27/3804; A61L 27/3895; A61L 27/60; G01N 33/56966
USPC .................................................. 424/93.7, 484
See application file for complete search history.

(56) References Cited

U.S. PATENT DOCUMENTS

| 5,591,444 A | 1/1997 | Boss, Jr. |
| 5,858,390 A | 1/1999 | Boss, Jr. |
| 6,124,522 A | 9/2000 | Schroeder |
| 6,533,819 B1 | 3/2003 | Urry et al. |
| 6,699,470 B1 | 3/2004 | Ameer et al. |
| 6,878,383 B2 | 4/2005 | Boss, Jr. et al. |
| 7,196,054 B1* | 3/2007 | Drohan et al. ..................... 514/2 |
| 2002/0018757 A1* | 2/2002 | Harichian et al. .............. 424/59 |
| 2002/0103542 A1* | 8/2002 | Bilbo ......................... 623/23.72 |
| 2002/0161440 A1 | 10/2002 | Son et al. |
| 2003/0069639 A1 | 4/2003 | Sander et al. |
| 2003/0165482 A1 | 9/2003 | Rolland et al. |
| 2004/0029095 A1 | 2/2004 | Lowel et al. |
| 2004/0031067 A1* | 2/2004 | Herlyn et al. .................... 800/9 |

(Continued)

FOREIGN PATENT DOCUMENTS

| DE | 4127570 | 2/1993 |
| DE | 10116362 | 10/2002 |

(Continued)

OTHER PUBLICATIONS

Geesin et al., "Regulation of Collagen Synthesis in Human Dermal Fibroblasts in Contracted Collagen Gels by Ascorbic Acid, Growth Factors, and Inhibitors of Lipid Peroxidation," *Exp. Cell Res.* 206:283-290, 1993.
Hansbrough et al., "Composite Grafts of Human Keratinocytes Grown on a Polyglactin Mesh-Cultured Fibroblast Dermal Substitute Function as a Bilayer Skin Replacement in Full-Thickness Wounds on Athymic Mice," *J. Burn Care & Rehab.* 14:485-494, 1993.
Neidert et al., "Enhanced Fibrin Remodeling In Vitro with TGF-β1, Insulin and Plasmin for Improved Tissue-Equivalents," *Biomaterials* 23:3717-3731, 2002.
Berfield et al., "Insulin-like Growth Factor I (IGF-I) Induces Unique Effects in the Cytoskeleton of Cultured Rat Glomerular Mesangial Cells," *The Journal of Histochemistry & Cytochemistry* 45: 583-593, 1997.

(Continued)

*Primary Examiner* — Janet Epps-Smith
(74) *Attorney, Agent, or Firm* — Norton Rose Fulbright US LLP

(57) ABSTRACT

The present invention relates to compositions and methods for tissue regeneration, particularly for treating skin lesions such as wounds. In one aspect, the invention provides a wound healing composition comprising living cells such as fibroblasts within a support matrix such as fibrin, in which the cells have a wound healing phenotype, and in which the composition is single layered and has been incubated for up to about 8 days to allow development of the wound healing phenotype. The compositions and methods of the invention are useful especially for assisting the process of wound healing, particularly chronic open lesions that are slow to heal or resistant to healing.

36 Claims, 2 Drawing Sheets

(56) References Cited

U.S. PATENT DOCUMENTS

Figure 1:
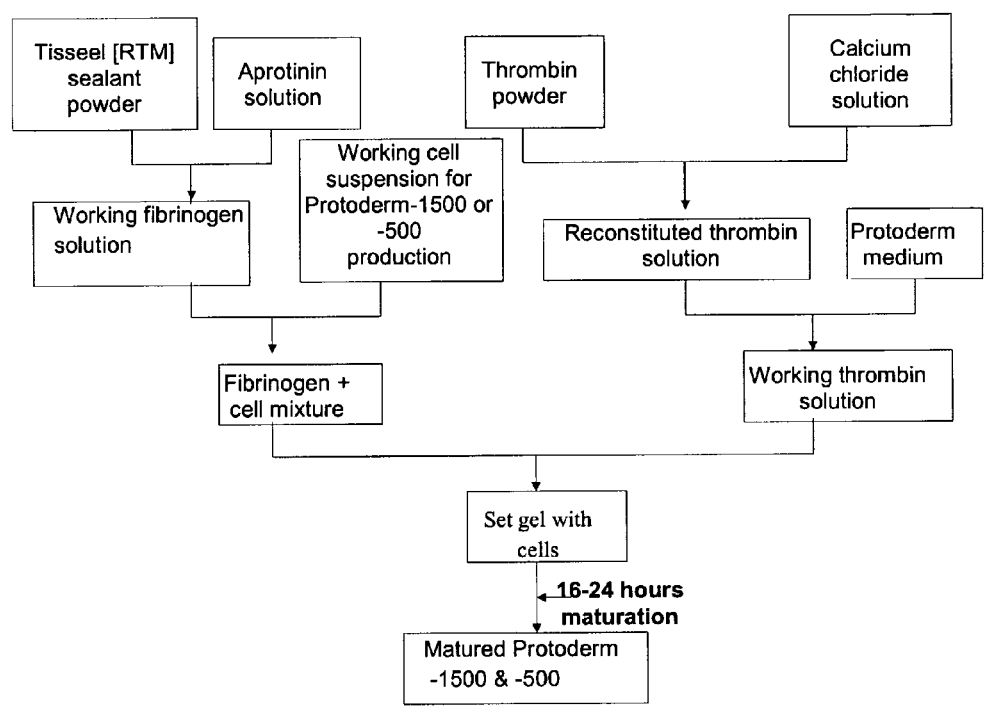

| | | |
|---|---|---|
| 2004/0082063 A1 | 4/2004 | Deshpande et al. |
| 2004/0162615 A1 | 8/2004 | Lam et al. |

FOREIGN PATENT DOCUMENTS

| | | |
|---|---|---|
| EP | 0 242 305 | 10/1987 |
| EP | 0 344 924 | 12/1989 |
| EP | 1 184 040 | 3/2002 |
| EP | 0 989 866 | 9/2002 |
| EP | 1358857 | 11/2003 |
| EP | 1 375 647 | 1/2004 |
| EP | 1 137 380 | 3/2004 |
| JP | 10-277143 | 10/1998 |
| RU | 2023424 | 11/1994 |
| RU | 2195889 | 1/2003 |
| RU | 2273457 | 4/2006 |
| WO | WO 98/36704 | 8/1998 |
| WO | WO99/15637 | 4/1999 |
| WO | WO 99/51164 | 10/1999 |
| WO | WO 01/32129 | 5/2001 |
| WO | WO02/072113 | 9/2002 |
| WO | WO 02/072800 | 9/2002 |
| WO | WO 02072113 A1 * | 9/2002 |
| WO | WO03/041568 | 5/2003 |
| WO | WO 03/084385 | 10/2003 |

OTHER PUBLICATIONS

Brown et al., "Fibroblast Migration in Fibrin Gel Matrices," *American Journal of Pathology* 142: 273-283, 1993.

Clark, "Regulation of Fibroplasia in Cutaneous Wound Repair," *The American Journal of the Medical Sciences* 306: 42-48, 1993.

Cullen et al., "The Differential Regulation and Secretion of Proteinases from Fetal and Neonatal Fibroblasts by Growth Factors," *Int. J. Biochem. Cell Biol.* 29: 241-250, 1997.

Eckes et al., "Impaired Wound Healing in Embryonic and Adult Mice Lacking Vimentin," *Journal of Cell Science* 113: 2455-2462, 2000.

Kessler et al., "Fibroblasts in Mechanically Stressed Collagen Lattices Assume a 'Synthetic' Phenotype," *The Journal of Biological Chemistry* 276: 36575-36585, 2001.

Kessler-Becker et al., "Expression of Pro-Inflammatory Markers by Human Dermal Fibroblasts in a Three-Dimensional Culture Model is Mediated by an Autocrine Interleukin-1 Loop," *The Biochemical Journal* 379: 351-358, 2004.

Meana et al., "Large Surface of Cultured Human Epithelium Obtained on a Dermal Matrix Based on Live Fibroblast-Containing Fibrin Gels," *Burns* 24: 621-630, 1998.

Muhart et al., "Behavior of Tissue-Engineered Skin: A Comparison of a Living Skin Equivalent, Autograft, and Occlusive Dressing in Human Donor Sites," *Arch. Dermatol.* 135: 913-918, 1999.

Neidert et al., "Fibrin as an Alternative Biopolymer to Type I Collagen for Tissue-Equivalent Fabrication," *Proceedings of the 2001 Bioengineering Conference* 50: 215-216, 2001.

Schäffer et al., "Nitric Oxide, an Autocrine Regulator of Wound Fibroblast Synthetic Function," *The Journal of Immunology* 158: 2357-2381, 1997.

Tuan et al., "In Vitro Fibroplasia: Matrix Contraction, Cell Growth, and Collagen Production of Fibroblasts Cultured in Fibrin Gels," *Experimental Cell Research* 223: 127-134, 1996.

Whiteside et al., "Heterogeneous Synthetic Phenotype of Cloned Scleroderma Fibroblasts May be Due to Aberrant Regulation in the Synthesis of Connective Tissues," *Arthritis and Rheumatism* 31: 1221-1229, 1988.

Office Communication, issued in Japanese Patent Application No. 2006-552692, dated Nov. 30, 2010. (English Translation).

Alderton, W. et al: "Regenerative medicine: A new frontier for therapeutic intervention. Highlights from the Society for Medicines Research Symposium", *Drugs of the Future*, 2010 vol. 35(6), pp. 517-521.

* cited by examiner

A

B

C

WOUND HEALING COMPOSITION

CROSS-REFERENCE TO RELATED APPLICATIONS

This application is the U.S. National Stage of International Application No. PCT/GB2005/000523, filed Feb. 14, 2005, which claims benefit from Great Britain Application No. 0403220.7, filed Feb. 13, 2004, Great Britain Application No. 0403226.4, filed Feb. 13, 2004, U.S. Provisional Application No. 60/556,194, filed Mar. 25, 2004, U.S. Provisional Application No. 60/556,155, filed Mar. 25, 2004, Great Britain Application No. 0426252.3, filed Nov. 30, 2004, and U.S. Provisional Application No. 60/632,425, filed Dec. 1, 2004, each of which is hereby incorporated by reference.

The present invention relates to compositions and methods for tissue regeneration, particularly for treating skin lesions such as wounds. The compositions and methods are useful especially for assisting the process of wound healing, particularly chronic open lesions that are slow to heal or resistant to healing.

Healing of open wounds extending through the germinal epithelium in otherwise healthy tissue takes place by the process classically described as "second intention", which, following initial haemostasis, involves a well-ordered sequence of inflammation, cellular infiltration, angiogenesis, granulation and re-epithelialisation. As part of the normal healing response, resident fibroblasts are required to undergo a series of phenotypic changes, migrating to the wound site, then proliferating, then synthesising and secreting extracellular matrix molecules. In vivo, a least a proportion of fibroblasts then switch to a myofibroblastic phenotype in order to facilitate wound contraction.

In vitro, a series of phenotypically distinguishable mitotic and post-mitotic fibroblast populations have been described (Bayreuther et al., 1988, Proc Natl Acad Sci USA 85: 5112-5116). The pathway of differentiation appears to be controlled, at least in part, by interactions between fibroblasts and extracellular matrix (ECM) proteins present at the wound site. Growth factors and cytokines undoubtedly also exert an important influence, although their effects too, appear to be modulated by fibroblast exposure to particular ECM proteins. Among the ECM proteins that appear to have an important role in fibroblast differentiation are fibrinogen and fibrin. Fibroblasts specifically interact with fibrin and fibrinogen "RGD" motifs through $\alpha_v\beta_3$ integrin receptors although the cellular response is complex and modulated by other factors. In vitro studies of the effect of fibrin glue on human periodontal ligament fibroblasts have suggested that fibrin appeared to slightly inhibit fibroblast proliferation. The presence of a fibrin matrix has also been reported to increase the synthesis of collagen by entrapped fibroblasts (Neidert et al, 2001, Proceedings of the ASME Bioengineering Conference, Kamm et al. [Eds], Vol 50: 215-216).

Fibroblasts are also known to have a role in the remodelling of fibrin clots. As new extracellular matrix proteins such as collagen type I and III, fibronectin and vitronectin are laid down, the fibrin matrix is broken down, predominantly by the activation of the plasma-derived enzyme plasmin. This is regulated by the activation (or inhibition) of its proenzyme, plasminogen, by a variety of plasminogen activators and inhibitors. In vivo, a number of infiltrating cells, such as neutrophils and macrophages, secrete urokinase-type plasminogen activator (uPA), whilst endothelial cells are largely responsible for producing tissue plasminogen activator (tPA). Fibroblasts also secrete both uPA and plasminogen activator inhibitors, such as plasminogen activator inhibitor-1 (PA-1). The balance between these antagonistic mediators is crucial in controlling fibrin remodelling and scar formation. The expression of the antagonistic mediators is developmentally regulated, as well as being controlled by extracellular matrix components and local growth factors.

To facilitate movement through a cross-linked fibrin clot and a tight meshwork of extracellular matrix, a variety of fibroblast- and serum-derived enzymes cleave a path for migration. These include interstitial collagenase (matrix metalloproteinase-1, MMP-1), gelatinase (matrix metalloproteinase-2, MMP-2), stromelysin (matrix metalloproteinase-3, MMP-3) and the plasminogen activators. Chemotactic factors such as TGF-β and PDGF may upregulate the production and secretion of these enzymes.

Once migrating fibroblasts reach a wound, they gradually become secretory and protein synthesis is increased. The previously retracted endoplasmic reticulum and Golgi apparatus becomes dispersed throughout the cytoplasm and a loose matrix is produced, which is mainly composed of fibronectin and type III collagen. Ultimately, this profibrotic phenotype takes over, which is characterised by an abundance of rough endoplasmic reticulum and Golgi apparatus, secreting newly synthesised collagen in response to highly expressed TGF-β. Notwithstanding, TGF-β fails to upregulate further collagen deposition, once a matrix has been deposited. It is also thought that IL-4 released by mast cells induces a modest increase in types I and III collagen together with fibronectin. Mast cells furthermore produce tryptase (a serine esterase) in abundance, which has been shown to upregulate fibroblast proliferation.

Stimuli such as TGF-α, TGF-β and PDGF responsible for fibroblast proliferation and matrix synthesis have been extensively investigated in vitro (Derynck, 1988, Cell 54: 593-595; Ross & Raines, 1990, In: Growth Factors: From genes to clinical applications, Sara et al. [Eds], pp. 193-199, Raven Press, New York; Sporn & Roberts, 1992, J Cell Biol 119: 1017-1021) and by in vivo manipulation of wounds (Sprugel et al., 1987, Am J Pathol 129: 601-613; Pierce et al., 1991, J Cell Biochem 45: 319-326). γ-interferon on the other hand was demonstrated to have a negative effect on the mitogenic and synthetic potential of fibroblasts in vitro and in vivo (Duncan & Berman, 1985, J Exp Med 162: 516-527; Granstein et al., 1987, J Clin Invest 79: 1254-1258). In addition, the collagen matrix itself can suppress these activities (Grinnell, 1994, J Cell Biol 124: 401-404; Clark et al., 1995, J Cell Sci 108: 1251-1261), whilst fibrin or fibronectin matrix have little or no suppressive effect (Clark et al., 1995, supra). Many fibroblasts undergo apoptosis (programmed cell death) in day-10 healing wounds, thereby marking the transition from a fibroblast-rich granulation tissue to a scar tissue with reduced cell density.

Where a wound has destroyed the germinal layer of epithelium, collagen deposition by infiltrating fibroblasts and re-epithelialisation results in a degree of scarring, with incomplete restoration of function in terms of the flexibility and elasticity of the original dermis and failure to regenerate auxiliary structures such as hair follicles and sweat glands.

A number of factors may adversely affect the rate and extent of such wound healing, in particular, poor blood supply. Poorly perfused tissue, often associated with impaired venous return and varicose veins, peripheral vascular disease or diabetes, often fails to heal satisfactorily, resulting in chronic ulcers, although the details of the pathogenesis are still unclear. Chronic leg ulcers in particular are a significant and growing problem world-wide.

Various approaches have been tried for the treatment of wounds. Autologous skin-grafting has been used to close open wounds, minimise the risk of opportunistic infection, accelerate healing and minimise scarring. Skin grafting has significant limitations, not least the requirement for a suitable donor site from which grafts can be taken which is a particular problem where wounds are extensive (for example, with burns). In addition, grafts have a low success rate where wound healing is compromised.

With respect to chronic leg ulcers in particular, the introduction of compression therapy in combination with moist wound dressings has been the standard therapeutic management.

More recently, tissue-engineering solutions have become available. Research into regenerative medicine has shown that human cells have substantial potential to heal and regenerate damaged tissue especially when primed by an environment that closely mimics the natural physiological condition being treated. Much of this research has focused on the production of so-called "tissue equivalents", which aim to provide a temporary functional replacement for missing tissue and accelerate healing. Tissue equivalents may be dermal equivalents or total skin equivalents, with the aim being to provide effective coverage of the wound as quickly as possible. The development and production of tissue equivalents usually involves the isolation of replacement skin cells, which are expanded and seeded onto or into a supporting structure such as a three-dimensional bioresorbable matrix, or within a gel-based scaffold.

A variety of materials have been used as acellular protein matrices for wound healing applications. These include synthetic polyesters (polyglycolic acid (PGA), polylactic acid (PLA), polyglactide (Dermagraft®, Smith & Nephew, described below), polydioxanone, polyhydroxyalkonoates and hyaluronic acid derivatives), hydrophilic polyurethanes (polyetherpolyester, polyethylene oxide and carboxymethylcellulose ethylene), and collagen-based scaffolds (cross-linked elastin collagen material (Mamiderm®), cross-linked collagens manufactured from acid-soluble type I bovine collagen material (such as Vitaphore®). An alternative approach is to use an acellular derivative of allogeneic human dermis, a natural dermal matrix from which cells have been removed (such as Allodern®, LifeCell Corporation). Some preparations use an organised, layered structure in order to more closely mimic the structure and function of the dermis. For instance, a preparation comprising an underlying layer of bovine collagen and shark glycosaminoglycans with an overlying layer of silicone is known (Integra®, Integra LifeSciences Corporation).

Other approaches to wound healing have involved the use of fibrin sealants, for example Tisseel® (Baxter), Beriplast® (Aventis), Quixil® (Omix Biopharmaceuticals), Haemaseel® (Haemacure) and Crosseal® (Omrix). These commercially available fibrin sealants are derived from cryoprecipitate of pooled plasma from virally-screened allogeneic donors.

Fibrin products rely on the natural polymerisation process that occurs during the physiological blood clotting cascade, in which a monomeric fibrin precursor, fibrinogen, is acted on by activated thrombin with the resultant production of polymeric fibrin. Fibrin forms the protein scaffold component of blood clots, to which platelets adhere.

Fibrin has been recognised as a convenient and clinically acceptable cell carrier to be used in tissue engineering applications. Commercially available products that utilise fibrin sealants for cell delivery include Bioseed® (Biotissue Technologies). The use of fibrin sealants for cell delivery purposes for the treatment burns has been suggested by several groups (see Brown et al., 1993, Am J Pathol 142: 273-283; Neidert et al., 2001, supra; Tuan et al., 1996, Exp Cell Res 223: 127-134; and US Patent Appl. No. 2003/01654482).

Exogenously applied dermal cells have been shown to have beneficial effects on wound healing including shorter time to complete healing (Falanga & Sabolinski, 1999, Wound Repair Regen 7: 210-207), delivery of active growth factors to the wound (Naughton et al., 1997, Artif Organs 21: 1203-1210), reduced potential for lesion recurrence (Gentzkow et al., 1996, Diabetes Care 19: 350-354), and reduced pain (Muhart et al., 1999, Arch Dermatol 135: 913-918).

Known combinations of protein matrices and dermal cells for wound healing applications include a preparation called Dermagraft® (Smith & Nephew) comprising cryo-preserved primary human foreskin fibroblasts seeded onto a bioabsorbable glycolic-lactic acid polyester (polyglactide) scaffold (Naughton et al, 1997, supra; U.S. Pat. No. 4,963, 489). The fibroblasts are allowed to proliferate in the scaffold, secreting extracellular matrix proteins and growth factors and cytokines. The mature preparation is packaged in 10% dimethylsulphoxide and bovine serum as a cryoprotectant to allow storage of the product by freezing prior to use. Disadvantages of this approach include difficulty in manipulating the product during application to the wound (such as ulcers), and the necessity of storing and transporting the product at very low temperatures ($-70°$ C.) and use of careful thawing procedures in order to ensure viability of the cells (see WO 87/06120).

Various combinations of collagen-based matrices and living cells are known. Apligraf® (Organogenesis, Inc.) is a bilayered structure comprising a lower ('dermal') layer of a bovine collagen scaffold supporting living human fibroblasts and an upper ('epidermal') layer comprising human keratinocytes on a collagen scaffold (Falanga & Sabolinski, 1999, supra; WO 99/63051). The preparation is supplied as a circular disk approximately 75 mm in diameter and 0.75 mm thick on an inert polycarbonate membrane. Apligraf® is packaged individually for use and has a 5-day shelf life. It is maintained in an agarose-rich nutrient with a 10% $CO_2$/air atmosphere and is shipped and stored at room temperature (20° C. to 31° C.; 68° F. to 88° F.). The removal of the product form the storage dish and polycarbonate membrane involves teasing away the edge of the Apligraf® using sterile forceps. Problems associated with this method include excessive folding which can make accurate, close application of the preparation to the wound difficult and time-consuming.

A similar product (Orcel®; Ortec International Inc) is described in U.S. Pat. No. 6,039,760. Orcel® is a bilayered structure of bovine collagen with fibroblasts and keratinocytes. The preparation is packaged between 2 non-adherent pieces of mesh, which are differently coloured to distinguish between sides. The device is then packaged in a plastic tray containing media to maintain cell viability during storage and shipping, which is further packaged into pouches with chill packs to maintain a temperature of 11° C. to 19° C. for 72 hours.

Another example of a tissue equivalent that attempts to reproduce a dermis-like arrangement of fibroblasts in a protein matrix supporting an overlying layer of keratinocytes is described in Meana et al. (1998, Burns 24: 621-630). Rama et al. (2001, Transplantation 72: 1478-1485) describe a method of culturing autologous limbal stem cells on a fibrin gel substrate for grafting to the contralateral cornea.

US Patent Appl. No. 20030165482 discloses a wound healing preparation (Allox®, Modex Therapeutiques SA) comprising growth-arrested allogeneic human fibroblasts and keratinocytes applied to a wound in a viscous paste of fibrinogen (Tisseel®) to which thrombin has been added, so that fibrinogen cleavage and fibrin polymerisation occur in situ. Alternatively, the separate liquid components are sprayed onto the wound, to set in situ, on mixing.

The present invention provides an alternative wound healing preparation and associated products and methods which address problems associated with prior art products and methods.

According to a first aspect of the present invention there is provided a wound healing composition comprising living cells within a support matrix, in which the cells have a wound healing phenotype, and in which the composition is single-layered and has been incubated for up to about 8 days to allow development of the wound healing phenotype.

The invention provides an approach to treatment of chronic wounds based, not on providing an immediately functional tissue-equivalent, but on delivering cells, in a support matrix (which could also be referred to as a maturation matrix or a development matrix; for example a biocompatible matrix), with the potential to promote and accelerate the healing process. Although developing a viable skin equivalent (for example, a cultured dermal tissue equivalent comprising fibroblasts, extracellular matrix and overlying keratinocytes organised into functional and anatomically relevant structures) remains a worthwhile goal, so far this has proven elusive. However, for many situations, the present invention shows that such an approach may be unnecessarily complex and that a simpler solution, that of providing a single layer of cells at the appropriate stage of development and exhibiting a particular phenotype in a wound-healing composition for rapid, convenient and accurate application to wounds, is remarkably effective. The cells used in the present invention develop surprising rapidly to have a "wound-healing phenotype" to encourage immediate wound healing. It is believed that the wound healing phenotype represents the optimal phenotype for accelerating or assisting wound healing. The invention allows delivery of such cells (in the composition) to a wound, preferably in a manner which is consistent with the maintenance of the wound-healing phenotype.

Whether or not cells in a composition have a wound healing phenotype may be tested by applying the composition to a wound (as defined herein) and observing whether or not healing of the wound is accelerated or assisted. Wounds to which the wound healing composition may be applied include wounds such as an ulcer such as a venous ulcer or a diabetic ulcer, a pressure sore, a burn or an iatrogenic grating wound. The composition is particularly useful for treating recalcitrant wounds, i.e. wounds which have not healed within three months using standard treatment.

The term "single-layered" indicates that the composition has only one layer containing cells within a support matrix, i.e. it is not a multi-layered "skin equivalent" with multiple layers of (different) cells. However, the invention also encompasses compositions having additional non-cellular layers as well as compositions having stacked layers comprising substantially uniform single layers.

The composition may be incubated for up to about 96 h, for example up to 72 h, 48 h, 25 h, or 24 h, preferably for 16 h to 24 h. Incubation is preferably in vitro, but may also be in situ (for example, with the composition applied to a wound).

In one embodiment, it has been found by the present inventors that taking cells such as passaged human dermal fibroblasts, casting (or seeding) the cells in a matrix such as a protein-based matrix and then incubating this mixture for up to 96 h, for example, results in a wound healing phenotype that is particularly beneficial for use in wound healing applications. It has been observed that such cells are predominantly in a proliferative phase in culture (encouraged by low density seeding, avoiding contact inhibition).

The present inventors have found that under normal culture conditions, for example, a liquid culture of human dermal fibroblasts incubated in a standard culture medium at 37° C., development of a wound-healing phenotype may typically take 2 to 3 days. However, incubation of such fibroblasts in a suitable environment such as in a support matrix and/or a wound shortens the development process, so that before 24 hours the cells may have entered or reached the wound-healing phenotype. Thus, incubation of cells in a suitable support matrix and/or wound results in a shorter development time to reach a wound healing phenotype than standard (for example, liquid) culture conditions.

The composition is preferably incubated at a temperature of about 37° C. If incubation takes place at a lower temperature, the living cells will develop at a slower rate and incubation time may need to be extended.

Preferably, the composition excludes mitotically inactivated cells (for example cells mitotically inactivated by administration of mitomycin C or other chemically-based mitotic inhibitors, irradiation with γ-rays, irradiation with X-rays, or irradiation with UV light, as described for example in US2003/0165482).

The composition may be stored after incubation (i.e. have a shelf-life) for up to about 40 days, preferably up to 28 days or 21 days or 19 days, and more preferably about 7 to 14 days or about 7 to 11 days at a temperature of 2° C. to 8° C., for example 3° C. to 5° C., preferably about 4° C., while retaining an ability to heal wounds. The composition therefore does not require freezing, as do certain prior art wound healing compositions. The present composition preferably does not contain a substance added as a cryopreservant or cryoprotectant (such as glycerol and/or human serum albumin).

Once the cells of the composition have been incubated to reach or approach a wound healing phenotype phase, the composition can preferably conveniently be stored at approximately 4° C. for up to 40 days, and certainly 7 to 14 days, before use without significant loss of viability or change of phenotype. This has significant practical advantages in that it provides not only an efficacious product comprising cells with a wound healing phenotype (for example cells that are optimally suited for secretion of extracellular matrix with minimal inappropriate fibrinolysis), but also gives a relatively long shelf-life under commonly available standard refrigeration conditions. The ability to ship such products at approximately 4° C. also considerably simplifies transportation. Maintaining a cold chain at 2° to 8° C. is considerably simpler and cheaper than shipping at −70° C., as is commonly required for live cells.

The cells are preferably mammalian, for example human.

Cells of the present invention may include fibroblasts, keratinocytes, stratum germinativum cells, and combinations or admixtures of such cells. However, in a preferred embodiment, the cells of the composition may substantially exclude keratinocytes. The cells may be isolated from any suitable mammalian source, and preferably are human. The cells are preferably allogeneic, although autologous and/or xenogeneic cells may be used. The cells may be substantially of one type only, for example 90% to 100%, preferably 95% to 99.5%, and more preferably 97.5% to 99% of one type. In a preferred embodiment, the cells are substantially fibroblasts, for example 90% to 100%, preferably 95% to 99.5%, and more preferably 97.5% to 99% fibroblasts. The fibroblasts may be dermal fibroblasts, preferably human dermal fibroblasts. A preferred embodiment comprises allogeneic human foreskin-derived fibroblasts.

As required for manufacture, cells may be thawed, recovered, expanded in culture (for example, for about a week) or until they reach confluence, and resuspended in appropriate volumes and densities as required. Although early passage cells are preferred, later passage cells may also be used. Preferably the cells have undergone less than 20 passages, more preferably less than 15 passages, most preferably less than 10 passages, for example 7 passages. Once defrosted for use in the present invention, the cells may be incubated further as described.

For the purposes of the present invention, day 0 is the day on which the cells are incubated and begin development and they will reach a wound healing phenotype within the time-frame described above (for example, up to 4 days, or 96 hours, after day 0).

The cells may be actively synthetic or able to become actively synthetic rapidly (for example, following storage).

The cells are preferably not proliferating and/or not senescent. Optimally the cells must be in a synthetic phase of development (or maturity), rather than a proliferative or senescent phase. Proliferation may be useful to increase cell numbers, but delays the important synthesis of extracellular matrix proteins such as collagen types I and III, fibronectin and vitronectin. Cells that have become senescent do not contribute to wound healing and so serve little purpose as such a therapeutic.

The cells may be suspended within the matrix, preferably substantially uniformly within the matrix.

The matrix may be protein-based, for example having a protein concentration in the range of about 3 to 12 mg·ml$^{-1}$. For example, the matrix is preferably a clottable or gelling substance such as fibrin, collagen, fibronectin, vitronectin, alginate, agar, collagen, PVA, hyaluronic acid, modified starches, carrageenans, carob, gelatine, pectin or gelling agent.

The matrix is preferably non-pyrogenic and/or sterile.

In a preferred embodiment, the matrix is a fibrin matrix. The fibrin may have a concentration in the composition in the range of 3 to 12 mg·ml$^{-1}$, for example 7 to 12 mg·ml$^{-1}$ or 3 to 5 mg·ml$^{-1}$. The fibrin matrix is preferably formed by thrombin-mediated polymerisation of fibrinogen.

The matrix is preferably solid or semi-solid. The matrix of the composition is "pre-cast" in the sense that it is provided as a solid or semi-solid form (such as a gel). The matrix may be insoluble. Most preferably, the cells are cast in the matrix prior to development of a wound healing phenotype.

The rate of fibrinolysis occurring within the composition may be a factor taken into account with a fibrin matrix-based composition. As described above, fibrinolysis is a normal part of the wound healing process, by which the fibrin matrix is gradually replaced by other extracellular matrix proteins. If, however, fibrinolysis occurs too early or too rapidly, the wound healing gel is broken down before useful collagen deposition has occurred. Fibroblast expression of pro-fibrinolytic factors such as urokinase-type plasminogen activator is developmentally regulated and so the phenotype of fibroblasts where included in the composition is relevant if premature fibrinolysis is to be avoided.

The wound healing composition may further comprise a protease inhibitor suitable for preventing breakdown of the matrix. The inhibitor may be a serine protease inhibitor, most preferably one or more selected from the list consisting of aprotinin, e-aminocaproic acid and tranexamic acid. Preferably, especially where the concentration of protein is in the range 7 to 12 mg·ml$^{-1}$, the protease inhibitor is aprotinin. Alternatively, especially where the concentration of protein is in the range 3 to 5 mg·ml$^{-1}$, the protease inhibitor may be tranexamic acid.

The composition may be incubated in a protein-rich environment.

Where the composition is sufficiently solid, it may be provided in any suitable shape and size, to suit the wounds it is design to be used with. Preferably, the composition is substantially disk-shaped. The composition may have a thickness of approximately 8 mm or less, preferably 5 mm or less. The thickness of the matrix will normally determine the thickness of the composition.

The wound healing composition may comprise about 450 to 2500 cells per mm$^2$, about 500 to 1500 cells per mm$^2$, about 750 to 2000 cells per mm$^2$, or about 900 to 1700 cells per mm$^2$ such as about 1450 to 1550 cells per mm$^2$ and preferably about 1500 cells per mm$^2$, or for example about 450 to 550 cells per mm$^2$ and preferably about 500 cells per mm$^2$, as measured per unit area. Lower cell densities than those indicated may result in poor cell viability. Higher cell densities may result in inhibition of extracellular matrix protein synthesis and progression to a senescent cell phenotype. Within the range of cell densities provided above, specific embodiments of the invention have been developed using approximately 500 cells per mm$^2$ and approximately 1500 cells per mm$^2$.

In a preferred embodiment, the wound healing composition comprises cells which are human dermal fibroblasts within a sterile, non-pyrogenic fibrin support matrix formed by thrombin-mediated polymerisation of fibrinogen, and in which the composition has been incubated for 16 to 24 h at about 37° C.

The composition may be packaged in a container suitable for transporting the composition (for example, while storing the composition) and/or topically applying the composition to a skin surface. The container may comprise a flexible pouch consisting of two sheets of impermeable flexible material peripherally sealed to provide a means of containment for the composition, the pouch comprising a first internal surface to which the composition is adherent at a level of adhesion more than that between the composition and a second internal surface of the pouch but less than that between the composition and the skin surface, such that in use the pouch may be opened by parting the sheets and the composition conveniently manipulated and directly applied to the skin surface without further requirement for the composition to be touched directly by any other means prior to application. For example, the container may be an Oliver® Products Company "Solvent Resistant Peelable Pouching Material" (Product number Q15/48BF1).

In a further aspect of the invention there is provided a wound healing composition as described herein for use as a medicament. For example, the composition may be for use as a medicament in the treatment of a skin lesion. The composition as a medicament may be used for topical application to a skin lesion or wound as described herein.

In a further aspect of the invention there is provided a method of manufacturing a wound healing composition as defined herein, comprising the steps of:

suspending living cells in a solution comprising a polymerisation agent and/or a monomer capable of being polymerised by the polymerisation agent into a matrix;

forming a single-layered support matrix comprising the cells by polymerisation of the monomer with the polymerisation agent; and incubating the matrix under conditions (for example, conditions as defined herein, such as temperature and time conditions) which allow development of a wound healing phenotype in the cells, thereby forming a wound healing composition.

Where for example the composition comprises monomer without polymerisation agent or polymerisation agent without monomer, the matrix may be formed by adding monomer or polymerisation agent as required to the solution such that both monomer and polymerisation agent are present in sufficient concentrations to effect polymerisation.

In another aspect of the invention there is provided a method of manufacturing a wound healing composition as defined herein, comprising the steps of forming a single-layered support matrix by polymerising a polymerisable monomer with a polymerisation agent, casting living cells into the support matrix, and incubating the matrix under conditions (for example, conditions as defined herein, such as temperature and time conditions) which allow development of a wound healing phenotype in the cells, thereby forming a wound healing composition.

Also provided is a method of manufacturing a wound healing composition, preferably a wound healing composition as described herein, comprising the steps of suspending living mammalian cells in a solution comprising a protein monomer capable of polymerisation into an insoluble matrix, adding an agent capable of promoting such polymerisation (i.e. a polymerisation agent) and allowing polymerisation to occur in a mould such that the solid polymerised composition may be removed from the mould and packaged ready for topical administration to a patient. The cells are preferably as described herein.

The monomer may be fibrinogen and the polymerisation agent may be thrombin. Alternatively, the polymerisation agent may be vitamin K-dependent clotting factors, venom serine proteases (for example, Crotalax, Batroxobin, Gabonase, Okinaxobin, Reptilase, Calobin and Fibrozyne) or other agents with thombin-like fibrinogen cleaving activity.

The cells may have a wound healing phenotype as described herein prior to being suspended in the monomer, or may adopt or develop into such a phenotype during incubation within the time-frames described herein (for example, within 0 h to 96 h after suspension).

Polymerisation may occur in a mould.

The methods may include steps adding additional components as described herein to the composition.

The method of the invention may comprise the further step of packaging the wound healing composition into a container for storing the composition and/or for transporting the composition and/or for topically applying the composition to a skin surface of a patient.

In a further aspect of the invention there is provided the use of living cells as defined herein in the manufacture of a wound healing composition as defined herein for the treatment of a skin lesion.

The invention also provides a method of treating a patient suffering from a skin lesion comprising topically applying of a wound healing composition as defined herein to the skin lesion.

In a further aspect, the invention provides a container (or package) for a solid or semi-solid, sterile, topical composition (preferably a wound healing composition as described herein) comprising a flexible pouch consisting of two sheets of impermeable flexible material peripherally sealed to provide a means of containment for the composition, the pouch comprising a first internal surface to which the composition is adherent at a level of adhesion more than that between the composition and a second internal surface of the pouch but less than that between the composition and a bodily surface to be treated, such that in use the pouch may opened by parting said sheets and the composition conveniently manipulated and directly applied to the bodily surface without any requirement for the medicament to be directly touched by any other means before application. The container per se aspect of the invention may exclude the Oliver® Products Company "Solvent Resistant Peelable Pouching Material" (Product number Q15/48BF1).

In a further aspect, there is provided use of a container as described herein for storing, transporting and/or applying a solid or semi-solid, sterile, topical composition (preferably a wound healing composition as described herein).

The container provides a convenient means of storage, delivery and application of any form of solid or, especially, semi-solid, materials, especially those intended for topical application to bodily surfaces. Preferably such materials are of a semi-solid or gel nature, such that physical manipulation would without the container be difficult. The preferential adherence of the material to an element of the container, with the ease of transfer thereafter to the skin or other bodily surface, provides a considerable advantage. In particular, such materials may be cut to the required size before application to the intended area. In the case of wound healing compositions as herein described, this is a particular advantage.

In a preferred embodiment, the container comprises metal foil, laminated or metalised plastic. In one preferred embodiment it comprises a transparent area allowing visual inspection of its contents.

Preferably, the internal surfaces of the container and its contents are sterile.

In a preferred embodiment, the first internal surface of the pouch is modified to increase the adherence of the composition thereto. In one embodiment this comprises application of a coating to the first internal surface. Preferably the coating is selected from the list consisting of: a polymer, a thermoplastic, a thermo-setting plastic, a protein, an amino acid, a carbohydrate.

Alternatively, the first internal surface is modified by roughening to increase the adherence of the composition thereto. As used herein, the term "roughening" includes any physical modification of the surface intended to improve adherence, such as embossing, scratching, abrading or scuffing, or chemical roughening by means of etching, erosion, acid or alkali treatment. Other means of modifying the surface energy properties of the surface in order to improve or modulate the degree of adherence of the solid or semi-solid product are disclosed. Such means include coating the first internal surface of the pouch. Preferably such a coating is selected from the list consisting of a polymer, thermoplastic, thermo-setting plastic, protein, amino acid or carbohydrate.

In one particularly preferred embodiment, the first internal surface is modified by means of a discontinuous coating, in the form of raised areas or dots, having the effect of providing a roughened surface.

Also provided according to the present invention is a method of packaging a sterile, solid or semi-solid topical composition as described herein comprising the step of placing the composition in a container pouch as described herein.

Figure 2:
Figure 2:
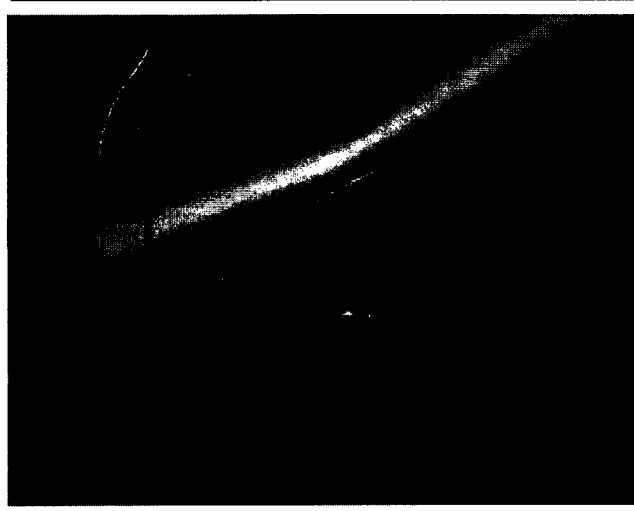
Figure 2:
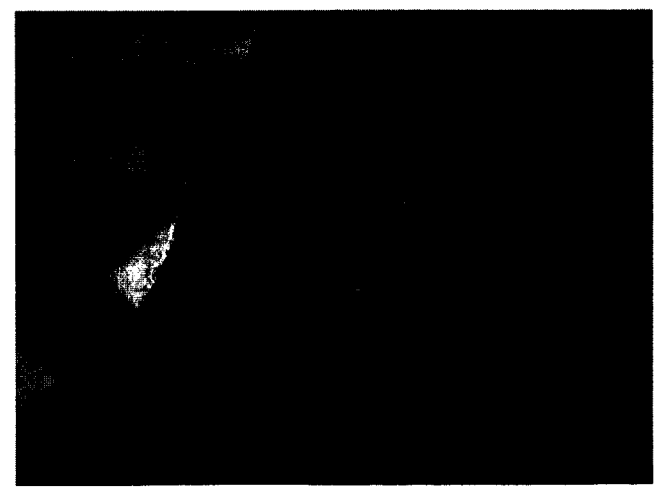

Specific examples of the invention will now be described with reference to the accompanying figures, in which:

FIG. 1 is a flow chart summarising a process of manufacturing a wound healing composition according to preferred embodiments of the invention; and FIG. 2 shows the packaging, manipulation and application of a preferred wound healing composition produced according to a process shown in FIG. 1. A: shows a matrix (or set gel) preferentially adhering to a modified internal surface of one of two metalised plastic sheets of a container pouch. B: shows the use of one of the sheets of the container to apply the gel of the wound healing composition to skin. Note that the sheet may used to support the gel while both are cut to the appropriate shape and size. C: shows the wound healing composition in place.

The process of manufacturing preferred compositions of the invention is summarised in FIG. 1. Alternative components or methods as described above may be used in place of those described here.

In principle, the composition comprises two components, which are cast together. The first component comprises a solution of fibrinogen together with one or more protease inhibitors to prevent unwanted proteolysis by protease contaminants and premature matrix breakdown by cells during storage. In particular, contaminants may include the naturally fibrinolytic enzyme plasmin, or its precursor plasminogen. Serine protease inhibitors such as aprotinin, e-aminocaproic acid, or its analogue tranexamic acid, are frequently used in order to inhibit plasmin or prevent its activation. Added to this fibrinogen solution is a suspension of living cells in a suitable medium or buffer solution (a "working cell suspension").

The second component comprises a solution of thrombin (an enzyme that naturally acts upon fibrinogen), calcium ions (a required cofactor), and a medium suitable for the culture of living cells. A further clotting factor, Factor XIII, is also activated by thrombin in the presence of calcium ions. Activated Factor XIII promotes polymerisation of monomeric fibrin (cleaved from fibrinogen by thrombin) into a three-dimensional protein insoluble scaffold.

In order to cast a gel (i.e. a matrix in the form of a gel), these two components are combined and, whilst still liquid, poured into a pre-coated suitable mould. Although commonly circular, the gels may be cast into any desired shape. For some applications, other shapes may be more suitable. In particular, essentially or substantially rectangular or elliptical gels may be more convenient for larger wounds.

Enzymatic cleavage of fibrinogen into fibrin monomers and polymerisation of these monomers results in setting of the liquid into a semi-solid gel in which living cells are suspended. For many applications, this gel is then maintained for a period of about 24 hours under suitable conditions for cell growth, division and secretion of extracellular matrix proteins, and other proteins such as growth factors. Following development (or maturation), the cast gel is removed from the casting mould and placed directly into a sterile package (which term is taken herein to have the same meaning as "container"). A small amount of medium, for example a buffer medium, is added to each package to maintain the product during storage and shipping, and the packages are sealed. During storage and shipping the packages are maintained at a temperature of 2° C. to 8° C.

In two preferred embodiments, called Protoderm 500 and Protoderm 1500, the composition comprises cells at a density of about 500 cells per $mm^2$ and about 1500 cells per $mm^2$, respectively.

Advantages of such a product over the currently available alternatives include the following. The use of a protein sealant as a scaffold or support matrix allows convenient topical delivery of cells to the wound. The pre-cast gel allows convenient and accurate application of regenerative cells to the wound surface with control of the distribution and density of cells applied. Manufacture and shipping of other tissue equivalents may take approximately 3 weeks for the matrix alone, whereas the product of the present invention may be manufactured within 10 days, or even as little as 2 days if sufficient growing cells are available. These factors combine to give cost advantages, so manufacture and production is more cost effective than many other commercially available products.

As described below, the product of the invention when packaged also features a unique flat pack system (adhesive backing) ensuring maintenance of product during shipping and "ease of use" of final product. The precast gels can be shipped and stored for up to 28 days at 2 to 8° C., whereas other available products must either be frozen or shipped at room temperature.

EXAMPLE 1

High Protein Concentration Product ('Protoderm 500' and 'Protoderm 1500')

A first embodiment of the invention is designed to optimise both rapid manufacturing of the wound healing product and rapid wound healing by containing cells and protein components at relatively high concentrations.

Matrix

In the first embodiment, the matrix protein is fibrin, derived from a commercial fibrinogen product, Tisseel® (Baxter). When reconstituted, this provides a convenient two component system to which cells may be added. Components of the matrix are summarised in Table 1. It should be noted that Tisseel® also contains Factor XIII, as well as plasmafibronectin and plasminogen.

TABLE 1

Primary components of Tisseel [RTM]

| Component | Final concentration in cellularised scaffolds |
|---|---|
| Matrix protein (fibrinogen) | 7.5-11.5 mg/ml |
| Aprotinin | 300 K IU/ml |
| Thrombin | 25 IU/ml |
| Calcium chloride | 4 mM |

As will be apparent to one of appropriate skill in the art, the concentrations of these components can be varied as required. For example, fibrinogen may be used in concentrations of the approximate range 7-20 $mg \cdot ml^{-1}$ for this application, thrombin in the range 5-50 IU/ml (in fact, trace levels of contaminating thrombin may lead eventually to fibrin formation and gel setting without additional thrombin, but this is inconvenient and unpredictable), and calcium chloride in the range 2-20 mM. Aprotinin is used to prevent unwanted fibrinolysis but, again, the exact concentration may be varied.

Cells

Human dermal fibroblasts were obtained by culture of cells derived from neonatal foreskin tissue. Under GMP (Good Manufacturing Practice) conditions, fibroblastic cells were isolated by collagenase digestion and expanded by culture and serial passage according to routine laboratory practice to establish a master cell bank (MCB). The MCB was screened against a panel of human and animal-derived viruses, bacteria, mycoplasma and fungi, and for tumorigenicity by a GLP (Good Laboratory Practice)-accredited facility and determined to be free of contamination. Several working cell banks (WCB) were then established for manufacture of the product, rescreened and stocks of cells frozen according to standard procedures.

It is also envisaged that for various patient-specific applications, autologous fibroblasts or other cells obtained from biopsies may be cultured and expanded for use.

The cells were suspended in the quantities shown below (P-500 refers to Protoderm-500; P-1500 refers to Protoderm-1500) in Liebowitz L-15 cell culture medium buffered and supplemented as shown in Table 2 before addition to the fibrinogen component. As will be apparent to one of skill in the art, medium not intended for use in a $CO_2$-enriched atmosphere (commonly used in tissue culture incubators or sealed flasks) must be appropriately buffered by some other system. Such media, supplemented with, for instance, HEPES, are well-known in the art. Liebowitz L-15 medium relies on a phosphate buffering system. The medium was supplemented with sodium bicarbonate and dextrose, as shown.

For convenience and consistency, a standard 'working cell suspension' of $1.5\times10^6$ cells.ml$^{-1}$ was generally prepared.

Preparation of Fibrin Sealant

As outlined in FIG. 1 and summarised below, Tisseel® thrombin powder was reconstituted in a calcium chloride solution according to the manufacturer's directions.

Once dissolved, the Thrombin/CaCl$_2$ solution was further diluted with supplemented L-15 medium to obtain a 'Working Thrombin Solution' and refrigerated until further use for a minimum of 15 minutes. (Gels may also be manufactured with 'Working Thrombin Solution' at room temperature.) Freeze-dried fibrinogen was reconstituted with an aprotinin solution before being added to the working cell suspension in supplemented L-15 medium. Once reconstituted, the fibrinogen should be used within 4 h, ideally within 1 to 2 h.

Working thrombin solution (6.75 ml) contains:
Thrombin: 501 U/ml (or 337.5 IU total)
Calcium chloride: 8 µmoles/ml (or 54 µmoles total)
In supplemented L-15
(Total Refers to the Amount in 6.75 Mls)
Working fibrinogen and cell suspension mix (total volume 6.75 ml):
Tisseel: 19 mg/ml (or 128.25 mg total)
Aprotinin: 600 KIU/ml (or 4050 KIU total)
Cells: $1.2\times10^6$ cell/ml ($8.1\times10^6$ cells total for P-1500); or $0.4\times10^6$ cell/ml ($2.7\times10^6$ cells total for P-500)
in supplemented L-15
(Total refers to the amount in 6.75 mls)

TABLE 2

Details of Medium Used for Example 1

| Components (Supplier shown in parentheses) | Function | Concentration per ml |
|---|---|---|
| L-15 medium (Cambrex) | Nutrient delivery to the cellular component of the product. Maintains cell viability and structure of the gel. | N/A (base medium) |
| Sodium Bicarbonate (Mallinckrodt Chemical) | Required for cell viability | 202.5 µg |
| Dextrose (J. T. Baker) | Nutrient | 4.5 mg |
| Adenine (ABCR) | Base required for cell viability | 24.4 µg |
| L-Glutamine (Molekula) | Amino acid for cell viability | 0.29 mg |
| Ethanolamine (Molekula) | Phospholipid for cell metabolism | 6.2 µg |
| O-phosphoryl-ethanolamine (Merck) | Phospholipid for cell metabolism | 14.12 µg |
| Hydrocortisone (Spectrum Laboratory Products, Inc.) | Steroid required for cell metabolism | 0.4 mg |
| Human Recombinant Insulin (Serologicals) | Essential hormone | 5 µg |
| Selenious acid (Molekula) | Trace substrate for metabolism | 6.78 ng |
| 3,3',5-Triiodo-L-thyronine (ABCR) | Hormone | 1.35 ng |
| apo-Transferrin, bovine (Serologicals) | Cofactor for iron metabolism | 5 µg |
| Gamma Irradiated Foetal Bovine serum or New Born calf serum (JRH or Hyclone) | Nutrients | 2% v/v |

Note: As will be apparent to one of ordinary skill in the art, sources of ingredients used to producing the wound healing composition may differ depending on the grade or purity required for different applications. For example, for clinical applications of the product, pharmaceutical grade materials may be required.

Casting the Gels

The working thrombin solution (6.75 ml) and Tisseel® fibrinogen/cell suspension mixture (6.75 ml) were combined by means of a Duplojet mixer unit and loaded into a suitable pre-coated casting container (conveniently a sterile Petri dish or similar) via a 16G needle or equivalent. It is useful to pre-coat the casting dish with serum containing media or albumin to prevent the gel from adhering. The gel set within a few minutes. The gel was then bathed in 20 ml of medium (Table 2) and the casting dish covered with a lid. The set gel was incubated at 37° C. for 16-24 hours to allow development (or maturation) of the cells.

Packing and Storage

After development (or maturation), the set gels were removed from their casting containers and placed into pre-irradiated, sterile foil pouches, stored within a sterile roto-seal bag. 10 ml serum-free medium (as per Table 2, without the foetal bovine serum) was added to each pouch before sealing. The shelf life of the sealed units is up to 28 days at 4° C.

EXAMPLE 2

Low Protein Concentration Product

For certain applications, it is possible to use lower protein concentrations. The chief advantage of this is reduction of production costs, since serum-derived proteins and many protease inhibitors, such as aprotinin, are expensive. In a preferred embodiment, the concentration of fibrin in the set product is reduced to less than 7 mg·ml$^{-1}$. In practice, 3.0-4.0 mg·ml$^{-1}$ is found to be effective.

One important consideration is the effectiveness (as well as the cost) of using aprotinin as protease inhibitor in such 'low protein' products. In particular, pro rata dilution of commercial products results in aprotinin concentrations that are too low to be effective. A preferable solution is to use an alternative inhibitor, such as tranexamic acid. Not only is this a highly effective inhibitor of fibrinolysis, but it has significant cost advantages.

Matrix

In this embodiment the matrix protein is fibrin, sourced from a commercial fibrin sealant, Tisseel®, using tranexamic acid instead of aprotinin. The key components of the matrix are summarised in Table 3. It should be noted that the same matrix composition could also be achieved using another commercially available fibrin sealant, Quixil. However the addition of exogenous tranexamic acid should be reduced as it already contains this inhibitor.

TABLE 3

Components of the Fibrinogen Matrix in Example 2

| Component | Final concentration in cellularised scaffolds |
|---|---|
| Matrix protein (fibrinogen) | 3.5 mg/ml |
| Tranexamic acid | 10 mg/ml |
| Thrombin | 25 IU/ml |
| Calcium chloride | 4 mM |

Freeze-dried Tisseel® fibrinogen is reconstituted with supplemented L-15 medium solution before being added to the working cell suspension in supplemented L-15 medium. Once reconstituted, Tisseel® fibrinogen should be used within 4 hours, ideally within 1-2 hours.

Tisseel® thrombin powder is reconstituted in a calcium chloride solution according to the manufacturer's directions. Once dissolved, the thrombin/CaCl$_2$ solution is further diluted with supplemented L-15 medium containing tranexamic acid to obtain a working thrombin solution.

The cell density used is again in the range 450 to 2500 cells mm$^2$. In order to minimise costs, it may be desirable to use a cell density of approximately 450 to 550 cells mm$^{-2}$. It should be noted, however, that protein concentration and cells density are independent variables. Lowering protein concentration is the major cost determinant, rather than cell density. However, being able to use fewer cells may have implications for the speed of production. In any case, high cell density/low protein concentration and low cell density/high protein concentration embodiments are envisaged and may be preferred in specific circumstances.

EXAMPLE 3

Packaging, Storage and Delivery

A major factor contributing to the success of topical wound healing compositions is the ease of accurately applying them to the wound surface so that a close contact is established, without air bubbles or creases, under sterile operating conditions. Wound healing compositions may be fragile, and handling should be kept to a minimum. The composition of the invention is preferably packaged in such a way as to significantly assist and facilitate application. In addition, the composition is shipped and stored chilled, rather than frozen, so that detailed thawing procedures are not required prior to use.

After setting and the 16-24 hour culture and development (or maturation) period, the individual gel discs are packaged by insertion into a flexible foil or metalised plastic pouch comprising two rectangular sheets, sealed along a substantial portion of three of their sides so as to form an open pocket. The inner surface of one of these sheets is modified so as to increase its adherence to the gel product. In a preferred embodiment as shown in FIG. 2, the packaging used is an Oliver® Products Company (Grand Rapids, Mich. USA) peelable foil pouch comprising one foil sheet and one sheet of laminated polyester/foil sheet with Q15 Adhesive dot pattern coating. Q15/48BF1 is a laminated lidding and pouching material for medical devices. The purpose of this dot pattern adhesive coating is to improve the efficiency of the heat sealing process which is used to seal the edges of the sheets together. However, the adhesive and raised dot pattern prove highly effective in providing a surface to which composition preferentially adheres, as compared with the smooth, uncoated inner surface of the opposing sheet. Other forms of coating and/or roughening of the surface of one of the internal surfaces of the pouch could be used to achieve the same effect. Similarly, any suitably durable, flexible, water and gas-impermeable sheet material might be used to manufacture such a pouch. All or part of the packaging might be transparent to allow visual inspection, for example, of the integrity of the composition or of the colour of a pH indicator dye in the cell culture medium, a small volume of which is inserted in the pouch, along with the composition, before the pouch is sealed along its remaining open edge.

Thus sealed, the composition has a shelf-life of at least 7-11 days, and preferably up to 28 days, more preferably 21 days, at 2° to 8° C.

For application, as shown in FIG. 2, the pouch is peeled apart, under sterile conditions, leaving the composition adhering to the treated inner surface of one of the sheets comprising the pouch. Using the sheet as a backing or means of support the composition is then applied to the surface of the wound, to which, in the absence of excessive exudation, it will preferentially adhere allowing it to be peeled away from the sheet. This means of application allows the composition to be applied without wrinkling or incorporation of air bubbles, and with the minimum of manipulation. The edges of the composition may be easily trimmed to fit the limits of the wound. Another advantage of delivering the composition in a format that is reversibly adherent to the packaging, as described, is that it allows the easy identification of the orientation of the product and facilitates oriented application, should this be required. In the case of a homogenous wound-healing product, orientation of the product on the wound is not important. However, where a multilayered composition is involved, such as one with a fibroblast layer that is intended to be applied in contact with the wound surface and a keratinocyte layer that is intended to be oriented away from the wound surface, it may be difficult or impossible to establish the orientation visually. In this case, the ability to deliver the product in such a way as makes incorrect application impossible without first removing the composition from the packaging offers a significant advantage.

The foregoing examples are meant to illustrate the invention and do not limit it in any way. One of skill in the art will recognise modifications within the spirit and scope of the invention as indicated in the claims.

All references cited herein are hereby incorporated by reference.

The invention claimed is:

1. A wound healing composition comprising living human dermal fibroblast cells suspended within a single-layered sterile, non-pyrogenic, solid or semi-solid, support matrix, said support matrix comprising a protein concentration of 3 to 12 mg·ml$^{-1}$ and a cell density of said human dermal fibroblasts of 450 to 2500 cells per mm$^2$, said cells having been incubated in the support matrix for 16 to 24 h at about 37° C.

2. The wound healing composition of claim 1, having been stored after incubation for up to about 40 days at a temperature of 2° C. to 8° C.

3. The wound healing composition of claim 1, in which the composition substantially excludes keratinocytes.

4. The wound healing composition of claim 1, in which the cells are actively synthetic or able to become actively synthetic rapidly.

5. The wound healing composition of claim 1, in which the cells are not proliferating or not senescent.

6. The wound healing composition of claim 1, in which the matrix comprises fibrin.

7. The wound healing composition of claim 6, in which the support matrix has a fibrin concentration in the range of 3 to 12 mg·ml$^{-1}$.

8. The wound healing composition of claim 6, in which the fibrin matrix has been formed by thrombin-mediated polymerisation of fibrinogen.

9. The wound healing composition of claim 1, further comprising a protease inhibitor.

10. The wound healing composition of claim 1, in which the composition has been incubated in a protein-rich environment.

11. The wound healing composition of claim 1, in which the composition has a thickness of approximately 8 mm or less.

12. The wound healing composition of claim 1, in which the composition is packaged in a container suitable for transporting the composition, storing the composition, or topically applying the composition to a skin surface.

13. The wound healing composition of claim 12, in which the container comprises a flexible pouch comprising two sheets of impermeable flexible material peripherally sealed to contain the composition, the pouch comprising a first internal surface to which the composition is adherent at a level of adhesion more than between the composition and a second internal surface of the pouch but less than that between the composition and the skin surface, such that in use the pouch may be opened by parting the sheets and the composition conveniently manipulated and directly applied to the skin surface without further requirement for the composition to be directly touched prior to application.

14. The wound healing composition of claim 12, in which the container is sterile.

15. The wound healing composition of claim 1, for use as a medicament.

16. The wound healing composition of claim 1, for use as a medicament in the treatment of a skin lesion.

17. The wound healing composition of claim 15, wherein said medicament is used for topical application to a skin lesion.

18. The wound healing composition of claim 2, in which the composition has been stored after incubation for up to about 19 days.

19. The wound healing composition of claim 18, in which the composition has been stored after incubation for about 7 to 14 days.

20. The wound healing composition of claim 2, in which the composition has been stored after incubation at a temperature of 3° C. to 5° C.

21. The wound healing composition of claim 20, in which the composition has been stored after incubation at a temperature of about 4° C.

22. The wound healing composition of claim 1, in which said human dermal fibroblasts comprise between about 90% to 100% of the cells of said composition.

23. The wound healing composition of claim 1, in which the cells are suspended substantially uniformly within the matrix.

24. The wound healing composition of claim 7, in which the support matrix has a fibrin concentration in the range of 3 to 5 mg·ml$^{-1}$ or 7 to 12 mg·ml$^{-1}$.

25. The wound healing composition of claim 9, wherein said protease inhibitor is aprotinin or tranexamic acid.

26. The wound healing composition of claim 11, in which the composition has a thickness of approximately 5 mm or less.

27. The wound healing composition of claim 17, wherein said skin lesion is a venous ulcer, diabetic ulcer, pressure sore, burn or iatrogenic grating wound.

28. The wound healing composition of claim 1, wherein the composition consists of living human dermal fibroblast cells suspended within a single-layered sterile, non-pyrogenic, solid or semi-solid, support matrix.

29. The wound healing composition of claim 1, wherein the composition comprises no additional cellular layers.

30. The wound healing composition of claim 1, wherein the composition comprises stacked layers comprising substantially uniform single layers.

31. A method for producing a wound-healing composition comprising living human dermal fibroblast cells, the method comprising:
   (i) suspending living human dermal fibroblast cells within a single-layered sterile, non-pyrogenic support matrix, said support matrix comprising a protein concentration of 3 to 12 mg·ml$^{-1}$; and
   (ii) incubating the suspended living human dermal fibroblast cells for 16 to 24 h at about 37° C. to achieve a cell density of human dermal fibroblasts of 450 to 2500 cells per mm$^2$.

32. The method of claim 31, further comprising storing the wound-healing composition before use for up to 40 days at a temperature of 2° C. to 8° C.

33. The method of claim 32, in which storing the wound-healing composition before use comprises storing the composition for about 7 to 14 days at a temperature of 3° C. to 5° C.

34. The method of claim 31, in which the support matrix comprises fibrin.

35. The method of claim 34, in which the support matrix has a fibrin concentration in the range of 3 to 12 mg·ml$^{-1}$.

36. The method of claim 31, further comprising applying the wound-healing composition to a venous ulcer.

* * * * *